(12) United States Patent  
Alphonse et al.

(10) Patent No.: US 7,680,378 B2
(45) Date of Patent: Mar. 16, 2010

(54) LOW REFLECTION LATERAL OUTPUT FIBER PROBE

(75) Inventors: Gerard A. Alphonse, Princeton, NJ (US); Mahesh Ajgaonkar, Plano, TX (US); Robert Comizzoli, Belle Mead, NJ (US); Rajeev Rohatgi, Pennington, NJ (US); Michael Nguyen, Philadelphia, PA (US)

(73) Assignee: Medeikon Corporation, Ewing, NJ (US)

( * ) Notice: Subject to any disclaimer, the term of this patent is extended or adjusted under 35 U.S.C. 154(b) by 0 days.

(21) Appl. No.: 11/684,680

(22) Filed: Mar. 12, 2007

(65) Prior Publication Data

US 2007/0292090 A1 Dec. 20, 2007

Related U.S. Application Data

(60) Provisional application No. 60/784,987, filed on Mar. 23, 2006.

(51) Int. Cl.
*G02B 6/06* (2006.01)
*G02B 6/02* (2006.01)

(52) U.S. Cl. .................. 385/119; 385/15; 385/117; 385/123

(58) Field of Classification Search .......... None
See application file for complete search history.

(56) References Cited

U.S. PATENT DOCUMENTS

| | | | |
|---|---|---|---|
| 4,962,988 A | 10/1990 | Swann | |
| 5,148,444 A | 9/1992 | Berger | |
| 5,831,743 A * | 11/1998 | Ramos et al. | 356/445 |
| 5,999,670 A | 12/1999 | Yoshimura et al. | |
| 6,446,713 B1 | 9/2002 | Insalaco | |
| 6,459,844 B1 | 10/2002 | Pan | |
| 6,501,551 B1 | 12/2002 | Tearney | |
| 7,057,158 B2 * | 6/2006 | Luo | 250/227.24 |
| 7,068,882 B2 * | 6/2006 | Saito et al. | 385/33 |
| 7,142,741 B2 * | 11/2006 | Osborne | 385/15 |
| 7,162,124 B1 * | 1/2007 | Gunn et al. | 385/37 |
| 7,189,007 B2 * | 3/2007 | Imanbayev et al. | 385/77 |
| 7,248,801 B2 * | 7/2007 | Fujita et al. | 398/141 |
| 7,341,384 B2 * | 3/2008 | Chan et al. | 385/89 |
| 2002/0041445 A1 | 4/2002 | Nichioka et al. | |
| 2002/0181123 A1 | 12/2002 | Han | |
| 2005/0165315 A1 | 7/2005 | Zuluaga et al. | |
| 2005/0281530 A1 * | 12/2005 | Rizoiu et al. | 385/146 |
| 2006/0067620 A1 | 3/2006 | Shishkov et al. | |

FOREIGN PATENT DOCUMENTS

JP 2002250842 A 9/2002

OTHER PUBLICATIONS

Alphonse et al., Mode Coupling in Angled Facet Semiconductor Optical Amplifiers and Superluminescent Diodes, IEEE J. Lightwave Tech. 10(2):215-219, Feb. 1992, vol. 10 No. 2.

* cited by examiner

*Primary Examiner*—Tina M Wong
(74) *Attorney, Agent, or Firm*—Pepper Hamilton LLP (57) ABSTRACT

A system and method which integrates a mirror at the fiber tip to the fiber tip and uses a tilted flat at the exit plane to prevent astigmatism caused by the cylindrical curvature of the fiber wall and minimize reflection.

24 Claims, 6 Drawing Sheets

LOW REFLECTION LATERAL OUTPUT FIBER PROBE

CROSS REFERENCE

This application claims priority from U.S. Provisional Application No. 60/784,987 entitled "Lateral Output Fiber Probe Having No Astigmatism and Low Reflection" filed Mar. 23, 2006 the contents of which are incorporated herein by reference in their entirety.

BACKGROUND

In medical cardiac diagnostics there is a need to detect and characterize plaques, lesions and other vascular pathologies and provide information to enable cardiologists to provide adequate therapy. Vulnerable plaques are a specific type of plaque that grows inside the artery and traps lipid within the arterial wall. Due to a natural defense mechanism in the body, such as the effect of macrophage, the thickness of the plaque can be eroded, and when it is down to about 65 microns or less, it is prone to rupture. This rupture releases the lipid into the blood stream and causes a thrombosis. Vulnerable plaque is a leading cause of death by sudden cardiac arrest. The resolution of state of the art technologies, such as MRI and IVUS, is limited to about 150 microns and does not enable measurements down to the critical thickness. The optical interferometric technique known as LCI (Low Coherence Interferometry) provides axial resolution capabilities approximately equal to the coherence length (which is about 10-20 microns with present-day superluminescent diode broadband sources) and therefore is suitable for the detection of vulnerable plaques. One way to construct an LCI instrument is to design an all-fiber interferometer and use the probing fiber component as part of a catheter. However, since the light in the fiber propagates along the fiber axis, some means is required to deflect the probing light toward the arterial wall.

Figure 1A:
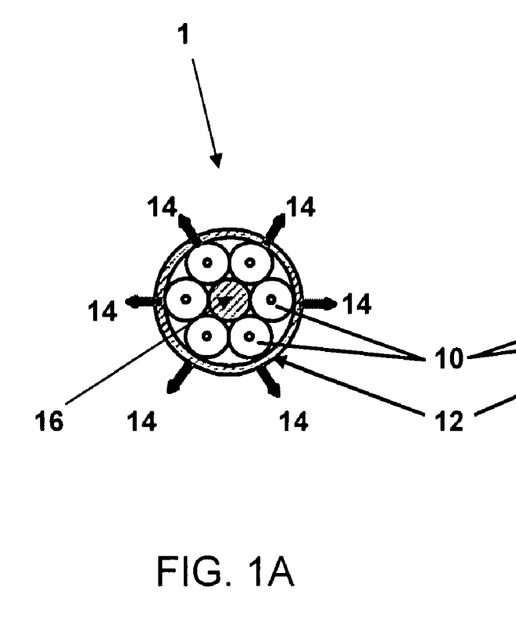
FIG. 1a illustrates a configuration with a center wire.
Figure 1B:
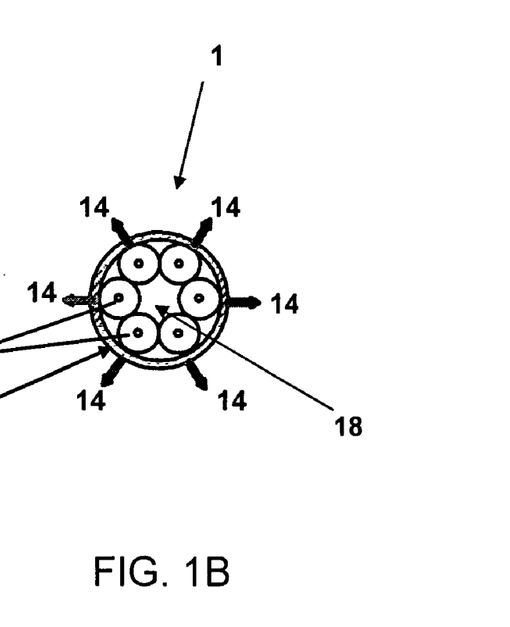
FIG. 1b illustrates a configuration without a center wire.

It is also desirable to probe several points around the circumference of an artery at the same time. By probing several points at the same time and pulling back the fiber along the length of the artery, one can examine a length of several centimeters of artery in a short period of time. FIGS. 1a and 1b for example, illustrate two configurations 1 for six fibers inside a one-French guide wire. The guide wire 12 is a flexible hollow tube commonly used in cardiac interventions using catheters that has an inner diameter of less than about 0.3 mm and an outside diameter of about 0.35 mm. Commercial corning SM (Single-Mode) fibers are available in 125-micron clad diameter and in about 80-micron clad diameter. The inner diameter of the guide wire is too small to accommodate six 125-microns diameter fibers, but it may accommodate six 80-micron fibers 10 of diameter 80-microns or less. Thus, while one may work with a smaller number of fibers or a guide wire larger than one-French, a preferred embodiment may be to use six fibers 10 at a time using a SM fiber having an 80-micron clad diameter. FIG. 1a illustrates a configuration with six fibers 10 around a center wire 16. FIG. 1b illustrates a configuration with a hollow central area 18 formed by the internal circumference of the six fibers 10.

Light being propagated through the optical fibers may then be deflected out of the guidewire as illustrated by the arrows 14. One manner in which to deflect the light by, for example, 90° is to grind and polish the fiber tip at 45° and coat the angled surface with a mirror. The resulting transmission through the cylindrical surface of the fiber clad, however, introduces astigmatism in the beam profile. For example, it transforms the beam from a Gaussian shape with a circular cross section in the fiber to one with a highly elliptical cross section. This causes it to spread out in one direction and reduces the backscattered light from the targeted direction, reducing the LCI signal by, for example, about 10 dB or more. Without the astigmatism, the LCI signal is some six orders of magnitude below the incident light from the fiber. The extra loss is not acceptable.

Figure 2:
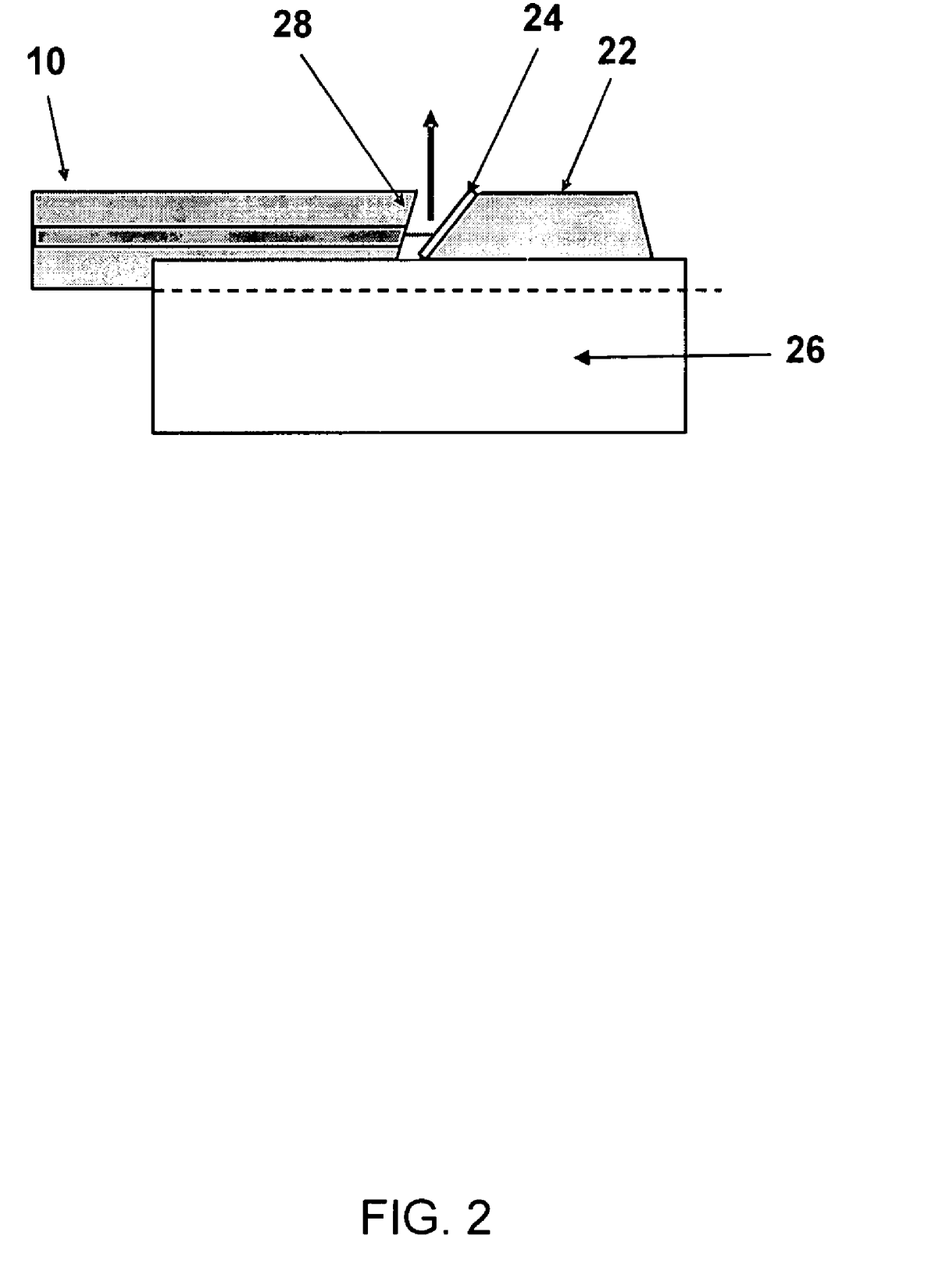
FIG. 2 illustrates a two-component probe.

The amount of reflection from the exit plane that is guided back to the detection system is also an important issue. With a high-power light source, it should be reduced as much as possible, preferably less than about −65 dB below the probing light level, in order to keep the so-called RIN (Relative Intensity Noise) below the optical shot noise. One approach to solve both the astigmatism and reflection issues may be to use two components, as illustrated in FIG. 2. This design includes a two component probe; a fiber probe 10 and a separate mirror 24 deposited on a section of similar fiber 22 ground and polished at, for example, 45°. Self alignment may be provided by mounting the two components in a grooved ferrule acting as an optical stage 26. Low fiber tip reflection may be obtained, for example, by cleaving (or cleaving, grinding and polishing) the fiber tip at an angle 28 as shown in FIG. 2, such that the reflected light is away from the fiber core. As an illustration, at normal incidence from a fiber-to-water interface, the reflection back into the fiber core is about −24 dB. With a single-layer AR (anti-reflection) coating on the fiber tip 28, it is decreased to about −35 dB. With an angle, most of the reflected light is away from the fiber core, and the amount of reflected light that is captured by the fiber core (the effective reflection) is below about −65 dB, even without AR coating. The back of the mirrored section 24 may be either ground at an angle or frosted to prevent partially transmitted light from being reflected back into the fiber. While a configuration of the ferrule 26 having a diameter of about 1.5 mm and length of about 3.5 mm preserves the beam profile, it is not suitable for placing several fibers inside a one-French tube.

Accordingly, there is a need for a system and method that prevents astigmatism and minimizes reflection in a fiber probe that can be used, for example, with multiple fibers in guide wire configurations with LCI.

SUMMARY

The invention described herein is directed to a reduced reflection, lateral output optical fiber. The optical fiber includes an optical emitting fiber, a mirror, and a tilted flat that may be tapered or flared. The optical emitting fiber includes a core and a cladding.

The mirror may, generally, be formed at an end of the optical emitting fiber adjacent to the tilted flat, and may be formed at an angle of about 45° as measured from a planar surface perpendicularly intersecting an axial centerline of the optical emitting fiber.

The tilted flat may, generally, be formed by removing the cladding around an exit plane or direction of light deflected by the mirror to provide a flat surface through which the deflected light may exit the optical emitting fiber. In embodiments, the tilted flat may have an angle of about 3° to about 12° measured from a planar surface parallel to an axial centerline and tangent to an outermost surface of the optical emitting fiber, and in some embodiments, the tilted flat may have an angle of about 8° measured from a planar surface parallel to an axial centerline and tangent to an outermost surface of the optical emitting fiber. The tilted flat of some embodiments may be covered, and certain embodiments may include a lens or an antireflection coating over the tilted flat. In particular embodiments, the tilted flat may include an anti-reflection coating.

In an optical fiber having a mirror and a tilted flat, a substantial portion of light reflected from the optical emitting fiber is not recaptured by the fiber core, and the light exiting the optical emitting fiber may also be substantially free of astigmatism.

In embodiments, for example, in biomedical applications, the optical fiber may be used in an optical probe LCI system for stent deployment.

The invention presented herein also includes a method for making a reduced reflection, lateral output optical fiber that includes providing an optical emitting fiber having a core and a cladding, forming a mirror at an end of the optical emitting fiber, and forming a tilted flat at an exit plane for light deflected by the mirror. The method may further include the step of forming a tilted flat by removing a portion of the cladding to provide a flat surface at the exit plane, and the exit plane may be at about 90° measured from an axial centerline of the optical emitting fiber.

The tilted flat, or embodiments, may have a tilt angle of about 8° measured from a planar surface parallel to an axial centerline and tangent to an outermost surface of the optical emitting fiber. In certain embodiments, the method may further include attaching a lens to the tilted flat and/or coating the tilted flat with an anti-reflective coating.

The present invention also includes a method for reducing reflection and astigmatism of light exiting an optical emitting fiber at an angle other than 0°. The method includes forming a mirror at an end of the optical emitting fiber, and forming a tilted flat at an exit plane for light deflected by the mirror. In some embodiments, the step of forming a tilted flat may include removing a portion of the cladding to provide a flat surface at the exit plane.

The tilted flat may have a tilted angle of about 8° measured from a planar surface parallel to an axial centerline and tangent to an outermost surface of the optical emitting fiber.

BRIEF DESCRIPTION OF THE DRAWINGS

For a better understanding of the disclosure and to show how the same may be carried into effect, reference will now be made to the accompanying drawings. It is stressed that the particulars shown are by way of example only, and for purposes of illustrative discussion of the preferred embodiments of the present disclosure only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIG. 1 illustrates two configurations of six fibers in a hollow guide wire.

DETAILED DESCRIPTION

Before the present devices, systems, and methods are described, it is to be understood that this invention is not limited to the particular processes, devices, or methodologies described, as these may vary. It is also to be understood that the terminology used in the description is for the purpose of describing the particular versions or embodiments only, and is not intended to limit the scope of the present disclosure which will be limited only by the appended claims.

It must also be noted that as used herein and in the appended claims, the singular forms "a", "an", and "the" include plural reference unless the context clearly dictates otherwise. Thus, for example, reference to an "artery" is a reference to one or more arteries and equivalents thereof known to those skilled in the art, and so forth. Unless defined otherwise, all technical and scientific terms used herein have the same meanings as commonly understood by one of ordinary skill in the art. "Optional" or "optionally" means that the subsequently described structure, event or circumstance may or may not occur, and that the description includes instances where the event occurs and instances where it does not.

As used herein, the term "about" means a practical engineering range near the target value. For example, such a range may be plus or minus 20% of the numerical value of the number with which it is being used. Therefore, about 50% means in the range of 45%-55%.

Unless otherwise indicated, the term "lesion" means an abnormal change in the structure of an organ or tissue as the result of injury or disease.

The term "plaque" may be taken to mean any localized abnormal patch on a body part or surface. In regard to arterial plaques, plaques may be fatty deposits on the inner lining of an arterial wall and are characteristic of atherosclerosis. The plaque may be an abnormal accumulation of inflammatory cells, lipids, and a variable amount of connective tissue within the walls of arteries. In part, embodiments of this invention are directed to the detection and treatment of plaques.

Although any methods and materials similar or equivalent to those described herein can be used in the practice or testing of embodiments of the present disclosure, the preferred methods, devices, and materials are now described. Nothing herein is to be construed as an admission that the invention is not entitled to antedate such disclosure by virtue of prior invention.

The present disclosure generally relates to a fiber probe, a system, and a method for minimizing reflection and preventing astigmatism in a fiber probe for use, for example, in a multiple-probe interferometer system. In particular, the disclosure relates to a fiber probe, system and method for minimizing reflection and preventing astigmatism in an optical emitting fiber.

As used herein, "optical emitting fibers" refers to optical fibers that are typically made of glass or a material having a higher dielectric constant than the surrounding medium. An optical emitting fiber generally has a core and a cladding. By core is meant the part of the optical fiber through which light is guided, and the choice of core size depends on the wavelength and numerical aperture, and on whether the fiber is intended to propagate light as a single waveguide mode or several waveguide modes. Typically, single-mode fiber core sized for wavelengths in the visible and near infra-red range may be about 5 to about 9 microns in diameter. Cladding is of a material having a lower refractive index than the core material and may surround the core to both ensure light guiding as well as to add mechanical strength to the fiber. The core and cladding of an optical fiber may be composed of any material through which light may pass including, but not be limited to glass, polymers, plastics, and combinations thereof.

Whether wave propagation in the fiber is single-mode or multimode is immaterial to the practice of the various embodiments of the disclosure. Hence, the term "optical emitting fibers" is also intended to include single-mode or multi-mode fibers. Single-mode fibers may be preferable for most applications, particularly those involving interferometry. The number of fibers used in a multiple fiber probe may be arbitrary. In a preferred embodiment, i.e., in which the fibers are contained inside a 1 French (0.014" diameter) guidewire, the number of fibers that may be utilized may be 1-12 optical fibers, more preferably 1-6 optical fibers, depending on the diameter of the optical fiber used. In other embodiments for example, where the fibers are housed in a catheter, the number of fibers can be larger, depending on the diameter of the catheter and the diameter of the optical fibers. For example, for a 1-mm diameter catheter with 80 micron diameter fibers embedded in the catheter wall, the number may be of the order of 30 optical fibers.

Figure 3:
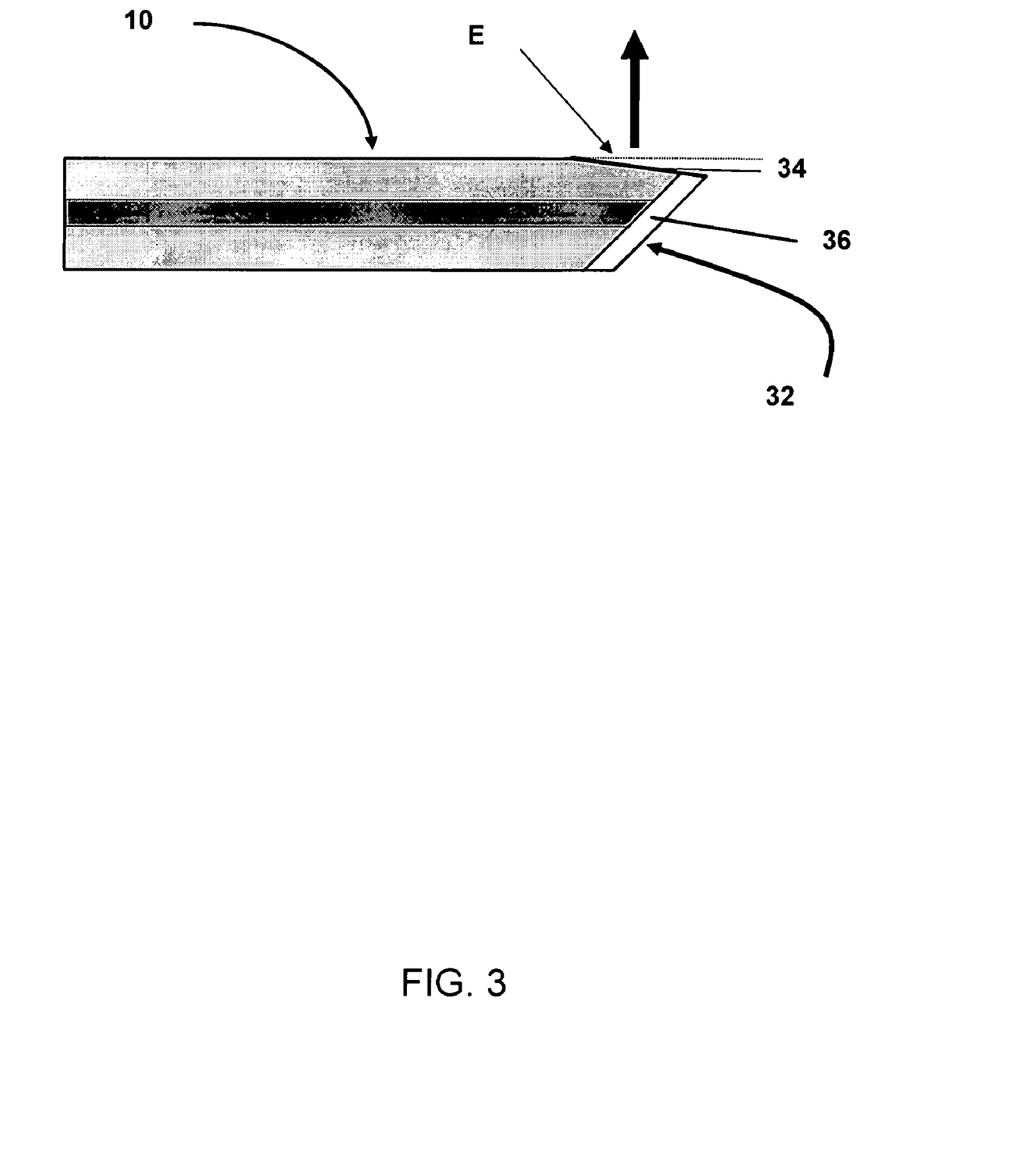
FIG. 3 illustrates a configuration of an output optical fiber in accordance with an embodiment of the present invention.
Figure 4:
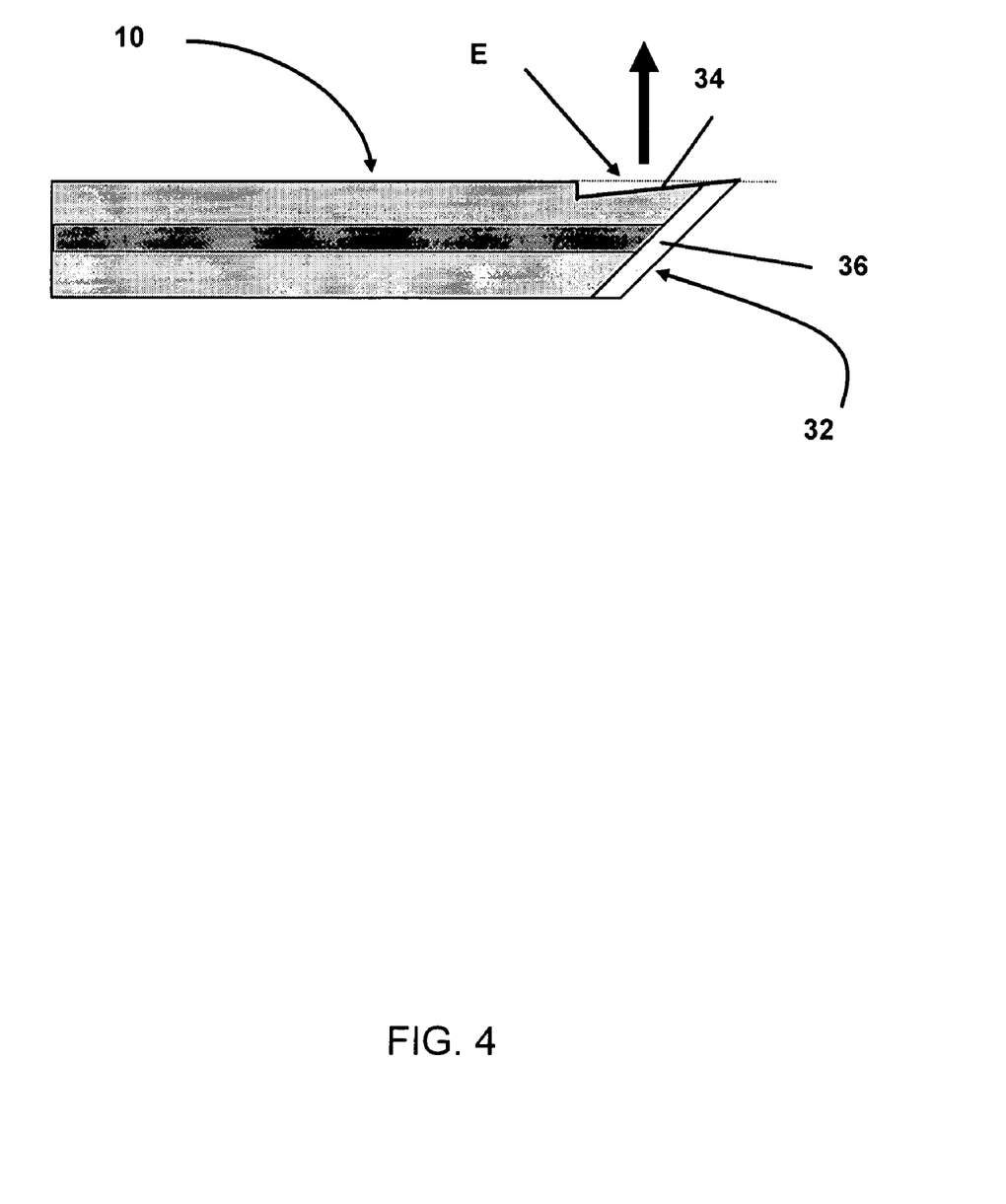
FIG. 4 illustrates another embodiment in accordance with the present invention.

As illustrated in FIGS. 3 and 4, and optical fiber 10 includes a fiber tip 32. The fiber tip 32 may include a mirror 36 integrated thereon, and a tilted flat 34. The tilted flat 34 is a ground and polished tilted flat at an exit plane E of the fiber probe. The flat portion of the tilted flat 34 acts to reduce or prevent astigmatism, and the tilt portion of the tilted flat 34 acts to prevent or reduce reflection. The tilted flat may be of any configuration. For example, FIG. 3 illustrates a tilted flat 34 having a taper configuration. Alternatively, as illustrated in FIG. 4, the tilted flat 34 may have a flare configuration.

The tilt angle may be configured so that light reflected from flat surface is directed away from the fiber tip 32 at the mirror and only a negligible portion of light is back-reflected from the tilted flat 34 and captured by the fiber tip 32. In general, the cone angle of the light beam emitted by a fiber tip 32 is roughly equal to the numerical aperture (NA) of the optical emitting fiber. For example, a typical single-mode fiber at 1300 nm wavelength may have an NA of 0.12 radians (equal to about 7°). By reciprocity, any reflected light incident upon the fiber tip 32 within that cone would re-enter the fiber tip 32. The tilted flat 34 may prevent such reentry. By the law of reflection, the magnitude of the reflection angle is equal to the magnitude of the incidence angle.

Figure 5:
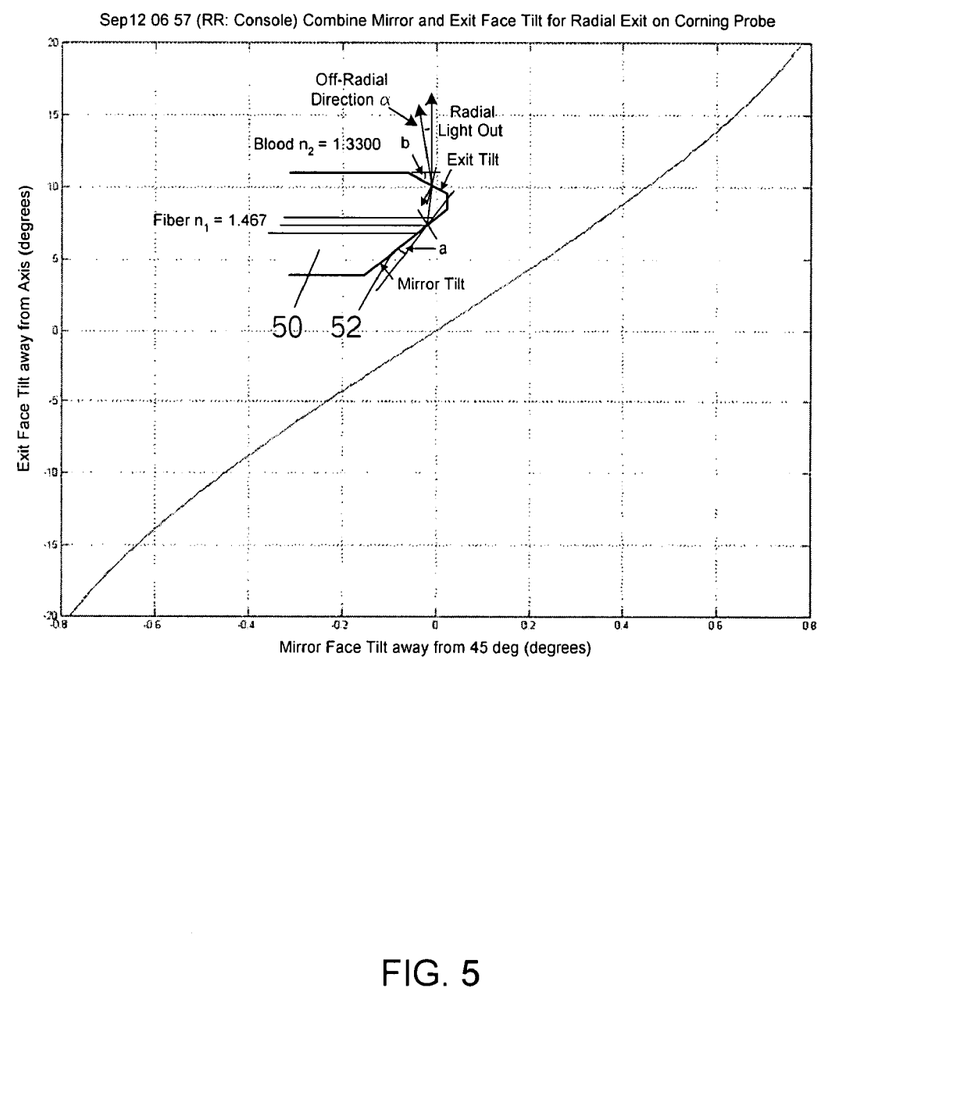
FIG. 5 illustrates a plot of relation between a tilt angle and a deviation of the mirror from 45° to ensure a radial output of the light in blood or water.

FIG. 5 illustrates the determination of the tilt angle of a titled flat 34. For a optical emitting fiber 50 having a mirror 52 positioned at a 45° angle at an end of the optical emitting fiber, the exit plane of reflected light, b, may be different from zero and the output angle may be off the radial direction by an amount α as specified by Snell's law (equation 1):

$$\alpha = \arcsin(n_1/n_2 \sin b) - b \qquad (1)$$

The radial output may be maintained by offsetting the mirror angle by an amount a from the 45° angle to reduce a to zero, and the relationship between the offset angle, a, and the tilt angle, b, may be given by equation 2:

$$a = \frac{1}{2}[b - \arcsin(n_2/n_1 \sin b)] \qquad (2)$$

A plot of the offset angle, a, and the tilt angle, b, for an interface between the edge of an optical emitting fiber having a refractive index $n_1$ of 1.467 and a medium having a refractive index for blood $n_2$ of 1.330 is provided in FIG. 5.

Table 1 shows the parameters for the above example (fiber-blood interface) as the tilt angle b is varied from about 4° to the critical angle of about 65°. The critical angle is the angle for total internal reflection between two media separated by the tilted interface. The first column in the table from left to right is the tilt angle, b, the second column is the refraction angle, the third column is the deviation, α, of the refraction angle from the radial direction, and the last column is the correction, a, to the mirror angle (from the 45° value) to reduce α to zero. All angles are in degrees. Similar tables can be derived for any other material systems having different values of $n_1$ and $n_2$.

TABLE 1

| Tilt angle 'b' | Refraction angle | α | a |
|---|---|---|---|
| 4 | 4.41 | 0.41 | 0.19 |
| 6 | 6.62 | 0.62 | 0.28 |
| 8 | 8.83 | 0.83 | 0.38 |
| 10 | 11.04 | 1.04 | 0.47 |
| 12 | 13.26 | 1.26 | 0.57 |
| 14 | 15.48 | 1.48 | 0.67 |
| 16 | 17.70 | 1.70 | 0.76 |
| 18 | 19.93 | 1.93 | 0.87 |
| 20 | 22.16 | 2.16 | 0.97 |
| 30 | 33.47 | 3.47 | 1.53 |
| 40 | 45.15 | 5.15 | 2.18 |
| 50 | 57.67 | 7.67 | 3.00 |
| 60 | 72.79 | 12.79 | 4.13 |
| 65 | 88.52 | 23.52 | 4.88 |
| 65.014 | 89.89 | 24.87 | 4.88 |

In practice, the correction, a, is not needed if the deviation, α, is within the divergence angle of the light beam. The beam divergence is about 7°, and a value of a less than about 2° is acceptable. By this criterion, for example, no correction may be needed if the tilt angle is less than about 20°. For larger tilt angles up to about 65°, an offset correction may be needed.

Adjusting the tilt angle of an optical emitting fiber may also reduce reflection by allowing index matching of the optical emitting fiber and the media through which the light travels eliminating the need for an anti-reflection coating on the optical fiber tip. Normally, the reflection coefficient between two media of refractive indices $n_1$ and $n_2$ is given by equation 3:

$$\left(\frac{n_2 - n_1}{n_2 + n_1}\right)^2 \qquad (3)$$

For the fiber-blood interface case, the reflection coefficient is about 0.24% or −26 dB. For many applications, this value may be too high and may be reduced by index matching. For example, a quarter-wave anti-reflection (AR) layer may be used for index matching. In the particular case of fiber and blood, the required index of the AR layer may be 1.4 which is not commercially available, and for interferometry using high-power broad band sources, a reflection below 0.01% or −40 dB is preferred. Tilting may achieve this index matching effect without the use of AR coatings. Thus, a tilt may be used to reduce the effective reflection to values that are below the normal index mismatch and that cannot be attained by an AR coating.

The effective reflectivity of the tilted flat depends on the optical mode profile, the refractive indices, the tilt angle, and the distance of the tilt plane from the fiber core. Calculations used for the design of superluminescent diodes using the tilted facets show that the reflectivity drops slowly for angles below about 4°, then drops rapidly for larger angles. [RE: G.

A. Alphonse and M. Toda, "Mode coupling in angled facet semiconductor optical amplifiers and superluminescent diodes", *IEEE J. Lightwave Tech*, Vol. 10, pp. 215-219, 1992]. For example, a rough calculation indicates that the reflectivity at 4° angle is of the order of 0.1% (or −30 dB) under conditions similar to the fiber-blood case, and a reflectivity of less than 0.001% or −50 dB may be achieved for an 8° tilt.

Therefore, in embodiments of the invention the tilt angle of the tilted flat may be at least about 4° to achieve a lateral output optical emitting fiber having a reflectivity of below about 0.1%, and a larger tilt angle may provide reflectivity of less than about 0.1%. The maximum allowed angle is the angle of total internal reflection between the input and output media, provided that adequate off-radial compensation is made by offsetting the mirror angle from the nominal 45° angle and is 65° and the maximum mirror offset is 4.88° for the optical fiber-to-blood system exemplified above. Finally, a tilt angle may be used at which mirror offset is not necessary wherein the output deviation from the radial direction is significantly less than the beam divergence angle. For example, a radial deviation of about 2° may be considered acceptable. For the fiber-to-blood system exemplified above, the tilt range for unnecessary correction is from about 4° to about 20°. In particular, an 8° tilt is adequate to provide a sufficiently low reflectivity with a 45° within a reasonable tolerance of less than ±1°. Accordingly, embodiments of the invention include lateral output optical emitting fibers having a tilt angle of from about 4° to about 65°, preferably from about 4° to about 20°.

In an embodiment, tilted flat 34 may be formed on an optical emitting fiber by removing a section of cladding material from an optical emitting fiber 10 at the exit surface E of light deflected by a mirror 36 formed at an end of the optical emitting fiber and processing that surface to a tilted flat from the fiber-clad normal exit surface. Without wishing to be bound by theory, a tilted flat 34 as described above may reduce or eliminate reflection and astigmatism of an optical fiber for lateral output of light, and the reduction or elimination of reflection and astigmatism may substantially reduce noise in the light signal propagated by the optical emitting fiber 10. In certain embodiments, lateral output optical emitting fibers having a tilted flat 34 to reduce reflection and astigmatism may be used in a multi-fiber optical probe 1 that may be used, for example, in LCI applications.

The tilted flat 34 of the present invention may also include a covering of any material known in the art that allows light to be transmitted through without altering, eliminating, or absorbing the light. Non-limiting examples of such materials include glass, polymers, plastics, and combinations thereof. The covering may be attached to the probe using any method known in the art including, but not limited to, optical cement, epoxy or other compounds capable of attaching the flat to the probe and the like. The covering may be a lens for the purpose of collimating or focusing the light to a certain distance. In other embodiments, the tilted flat 34 may be coated with an anti-reflective coating which may further reduce reflection of light exiting the optical emitting fiber back into the optical emitting fiber 10.

The mirror 36 on the fiber tip may be made by any means familiar to the art and may be, but is not limited to, an evaporated metal, or a multi-layer interference mirror made from two or more dielectrics. In general, a mirror may be placed at an end of an optical emitting fiber, and an angle at which the mirror 36 is ground may be measured from a planar surface perpendicularly intersecting an axial centerline of the optical emitting fiber. The mirror may be ground at an angle and may deviate slightly from the desired angle in one direction or another in order to compensate for the effect of the tilt on the radial output of the fiber. For example, in an embodiment, the mirror 36 may be ground at an angle which deviates slightly from 45° to allow light to exit the fiber at an angle of about 90° as measured from the axial centerline of the optical emitting fiber 10.

FIG. 5 illustrates a plot of the relationship between the mirror angle and the tilt angle to meet this condition modeled for a fiber having a modal index of 1.467 and for blood having an index of 1.330. The x-axis represents the mirror 36 deviation angle "a" and the y-axis represents the tilt angle "b". Although the sketch shows only a tapered embodiment, the formula may be used for a flared embodiment or other embodiment as well. For example, for an 8 degree tilt, the deviation of the mirror 36 from about 45° is only about 0.38 degree. Without implementing the about 0.38 degree deviation, the offset from the radial direction would be only about 0.83 degree, which may be insignificant in practice.

An embodiment of the disclosure includes laterally deflecting light from a fiber probe while minimizing reflection and reducing or preventing astigmatism from the exit plane of the fiber probe, and in certain embodiments, the fiber probe may be used in a probe system. For example, a catheter or guidewire having one or more lateral output fiber probes of embodiments may be used to probe an arterial lumen and to measure dimensions of the arterial lumen and accurately deploy a stent into the region. In some embodiments, the catheter device may include a plurality of lateral output optical emitting fibers which may be contained within a guidewire structure or within the catheter structure. The guidewire may be about 0.014" in diameter which is representative of current guidewire sizes used for coronary applications as understood by one skilled in the art. Alternatively, the size of the guidewire may vary depending on the desired application. For example, a guidewire and optical emitting fibers may be contained within a balloon catheter. The balloon catheter may be a hollow tube that is introduced over the guidewire. The unexpanded balloon catheter may be approximately 1 mm in diameter for coronary applications. A corresponding sized stent may then be deployed over the balloon catheter.

Another embodiment of the disclosure is directed to a method for determining a size of a vessel lumen by use of optical radiation. The method may be an interferometric method that includes utilizing optical radiations of coherence length, for example, shorter than approximately 20 μm, or in some embodiments, less than about 10 μm. The resolution (the ability to distinguish adjacent features) of an interferometer is determined by the coherence length of the light source. For example, a light source having a coherence length of 20 μm provides for a resolution of about 20 μm. The LCI reflected signal, which allows the size determination of an artery, may also be used to determine the linear distance of the optical emitting fiber to a stent being deployed on a balloon, as well as a linear distance to the lumen wall. These linear dimensions, which are obtained by analysis of specular reflections received by the optical emitting fibers allows for the determination of a cross-sectional area, and from that area, the diameter to which a stent should be expanded.

A further embodiment of the disclosure is a method of using received reflections from within an artery and calculating dimensions from such data to determine the size of a stent expansion in real time as well as the size of the lumen. By use of feedback or other signal processing in real-time, stent expansion may be stopped during a process when a desired expansion size is achieved without exceeding a maximum diameter of the lumen. For example, the stent expansion may be controlled manually by a physician or alternatively may be controlled by an automated software system. Additionally, the software system may include a fail safe mechanism, whereby expansion of a stent cannot exceed a maximum size, the maximum size being the measured diameter of the lumen of the artery.

Figure 6:
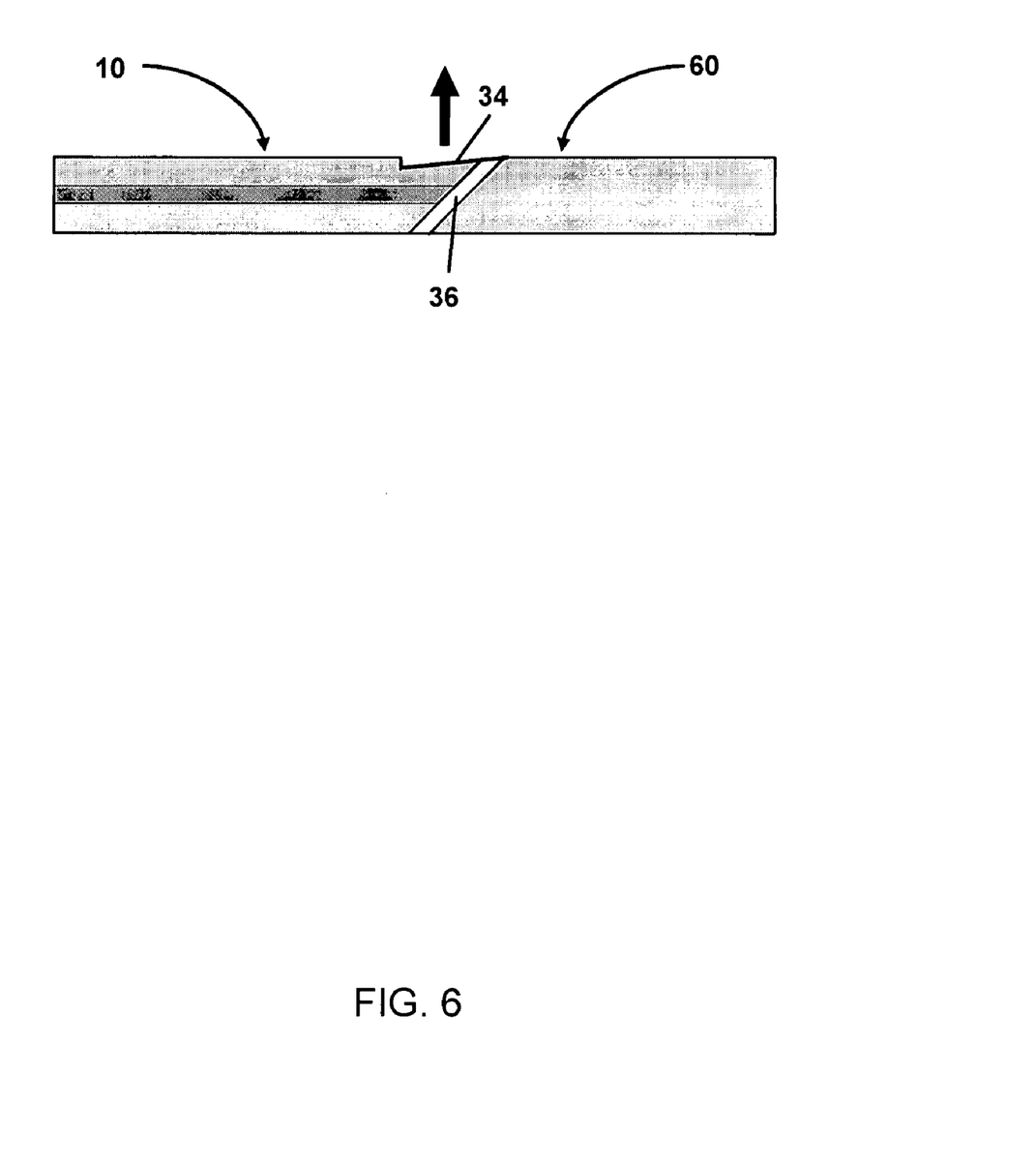
FIG. 6 illustrates another embodiment of the present invention featuring either type of tilted flat.

FIG. 6 illustrates an additional embodiment, featuring either type of tilted flat 34. This embodiment may be obtained by seamlessly attaching an extra section of fiber 60 to the probe 10. Although optical cement, epoxy or any other method familiar to the art may be used for attaching the extra section 60, fusion splicing may be used in order to maintain the same overall diameter of the main fiber without the use of excess material. This design provides for making a probe with the capability of bringing the fiber exit surface close to the arterial wall to reduce the propagation distance through blood. Propagation through blood may reduce the amount of backscattered signal from the arterial sample under examination.

It is appreciated that certain features of the invention, which are for clarity, described in the context of separate embodiments, may also be provided in combination in a single embodiment. Conversely, various features of the invention, which are for brevity, described in the context of a single embodiment, may also be provided separately or in any suitable sub combination.

It will be appreciated by persons skilled in the art that the present invention is not limited to what has been particularly shown and described hereinabove. Rather the scope of the present invention is defined by the appended claims and includes both combinations and sub combinations of the various features described hereinabove, as well as variations and modifications thereof, which would occur to persons skilled in the art upon reading the foregoing description.

What is claimed is:

1. A reduced reflection, lateral output optical fiber comprising:
    an optical emitting fiber having a core and a cladding;
    a mirror positioned to deflect light from the core laterally through the cladding; and
    a tilted flat formed on the cladding around an exit plane of the deflected light, wherein the tilted flat is tapered or flared with respect to a planar surface parallel to an axial centerline of the optical emitting fiber.

2. The optical fiber of claim 1, wherein the mirror is formed at an end of the optical emitting fiber and is adjacent to the tilted flat.

3. The optical fiber of claim 2, wherein the mirror is formed at an angle of about 45° as measured from a planar surface perpendicularly intersecting an axial centerline of the optical emitting fiber.

4. The optical fiber of claim 2, wherein the mirror deviates from a 45° angle to reduce reflection from a tilted flat having a tilt angle greater than about 20°.

5. The optical fiber of claim 1, wherein the tilted flat provides a flat surface through which the deflected light exits the optical emitting fiber.

6. The optical fiber of claim 1, wherein the tilted flat has a tilt angle such that reflectivity of the tilted flat back into the optical emitting fiber is lower than reflectivity from a flat with no tilt angle and/or having no anti-reflective coating.

7. The optical fiber of claim 1, wherein the tilted flat has an angle of about 4° to about 65° measured from the planar surface parallel to the axial centerline and tangent to an outermost surface of the optical emitting fiber.

8. The optical fiber of claim 1, wherein the tilted flat has an angle of about 4° to about 20° measured from the planar surface parallel to the axial centerline and tangent to an outermost surface of the optical emitting fiber.

9. The optical fiber of claim 1, wherein the tilted flat has an angle of about 8° measured from the planar surface parallel to the axial centerline and tangent to an outermost surface of the optical emitting fiber.

10. The optical fiber of claim 1, further comprising a covering over the tilted flat.

11. The optical fiber of claim 1, further comprising a lens over the tilted flat.

12. The optical fiber of claim 1, further comprising an anti-reflection coating on the tilted flat.

13. The optical fiber of claim 1, wherein a substantial portion of light reflected from the optical emitting fiber is not recaptured by the fiber core.

14. The optical fiber of claim 1, wherein light exiting the optical emitting fiber is substantially free of astigmatism.

15. The optical fiber of claim 1, wherein the optical fiber is used in an optical probe LCI system for stent deployment.

16. A method for making a reduced reflection, lateral output optical fiber comprising:
    providing an optical emitting fiber having a core and a cladding;
    forming a mirror at an end of the optical emitting fiber, said mirror being positioned to deflect light from the core laterally through the cladding; and
    forming a tilted flat on the cladding at an exit plane for light deflected by the mirror wherein the tilted flat is tapered or flared with respect to a planar surface parallel to an axial centerline of the optical emitting fiber.

17. The method of claim 16, wherein the step of forming a tilted flat comprises removing a portion of the cladding to provide a flat surface at the exit plane.

18. The method of claim 16, wherein the exit plane is at about 90° measured from the axial centerline of the optical emitting fiber.

19. The method of claim 16, wherein the tilted flat has a tilt angle of about 8° measured from the planar surface parallel to the axial centerline and tangent to an outermost surface of the optical emitting fiber.

20. The method of claim 16, further comprising attaching a lens to the tilted flat.

21. The method of claim 16, further comprising coating the tilted flat with an anti-reflective coating.

22. A method for reducing reflection and astigmatism of light exiting an optical emitting fiber at an angle other than 0° comprising:
    forming a mirror at an end of the optical emitting fiber, said mirror being positioned to deflect light from the core laterally through the cladding; and
    forming a tilted flat on the cladding at an exit plane for light deflected by the mirror, wherein the tilted flat is tapered or flared with respect to a planar surface parallel to an axial centerline of the optical emitting fiber.

23. The method of claim 22, wherein the step of forming a tilted flat comprises removing a portion of the cladding to provide a flat surface at the exit plane.

24. The method of claim 22, wherein the tilted flat has a tilt angle of about 8° measured from the planar surface parallel to the axial centerline and tangent to an outermost surface of the optical emitting fiber.

* * * * *